United States Patent [19]

Sheldon et al.

[11] 4,110,363

[45] Aug. 29, 1978

[54] PREPARATION OF ESTERS

[75] Inventors: Roger A. Sheldon; Peter Been, both of Amsterdam, Netherlands

[73] Assignee: Shell Oil Company, Houston, Tex.

[21] Appl. No.: 765,187

[22] Filed: Feb. 3, 1977

[30] Foreign Application Priority Data

Mar. 1, 1976 [GB] United Kingdom ............... 8045/76
Mar. 1, 1976 [GB] United Kingdom ............... 8046/76

[51] Int. Cl.$^2$ .................. C07C 120/00; C07C 121/66
[52] U.S. Cl. ............................................. 260/465 D
[58] Field of Search .................................. 260/465 D

[56] References Cited

U.S. PATENT DOCUMENTS 3,835,176 9/1974 Matsuo et al. .................. 260/465 D

OTHER PUBLICATIONS

Zymalkowski et al., *Arch. Pharmaz. Ber. Pharmaz. Ges.*, 62, No. 5, pp. 218–224, (1956).
Francis et al., *J. Chem. Soc.*, 95, pp. 1403–1409, (1909).
Kinder et al., *Arch Pharm.*, 271, pp. 431–439, (1933).
Coronyn, *J. Org. Chem.*, 14, pp. 1013–1022, (1949).
Fisher et al., *J. Org. Chem.*, 24, pp. 1650–1654, (1959).

*Primary Examiner*—Dolph H. Torrence

[57] ABSTRACT

Certain carboxylic acid esters also containing a cyano group are prepared by reacting an acid halide, an aldehyde and a water soluble cyanide in the presence of a water-immiscible aprotic solvent and a macrocylic polyether catalyst.

29 Claims, No Drawings

PREPARATION OF ESTERS

BACKGROUND OF THE INVENTION

1. Field of the Invention

The invention relates to a process for the preparation of certain cyano-substituted-carboxylic acid esters by reacting an acid halide, an aldehyde and a water-soluble cyanide.

2. Description of the Prior Art

According to U.S. Pat. No. 3,835,176, addition of substituted cyclopropanecarbonyl halides and m-substituted benzaldehydes, if necessary dissolved in an aprotic solvent, to an aqueous solution of sodium cyanide or potassium cyanide and stirring of the mixture obtained until no more conversion takes place, afford the desired esters. The experiment described in Example 4 of the above U.S. patent was conducted in the absence of a solvent, with an unsaturated aqueous solution of sodium cyanide, with a 20% molar excess of the cyclopropanecarbonyl halide (calculated on aldehyde) and at a temperature of 0° C.

Such a process has the disadvantages that the yield of the ester is relatively low and that keeping the temperature at 0° C and using the said molar excess are expensive.

The present invention obviates these disadvantages.

SUMMARY OF THE INVENTION

The present invention is directed to a process for the preparation of an ester formula I

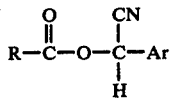

(I)

wherein Ar is an optionally substituted aromatic group, and R is an optionally substituted acyclic or saturated cyclic hydrocarbyl group, by contacting an aromatic aldehyde of the formula ArC(O)H and an acyl halide of the formula RC(O)Hal, in which formulas Ar and R have the same meanings as in formula I and Hal is a halogen atom having an atomic number of from 9 to 53, inclusive, with water, a water-soluble cyanide, a substantially water-immiscible aprotic solvent and a macrocylic polyether phase transfer catalyst.

Suitable phase transfer catalysts are macrocyclic polyethers known as "crown ethers." These compounds, together with their preparation, are described in the literature, for example in Tetrahedron Letters No. 18(1972) pp. 1793–1796, and are commonly designated by reference to the total number of atoms forming the macrocyclic ring together with the number of oxygen atoms in that ring. Thus the macrocyclic polyether whose formal chemical name is 1,4,7,10,13,16-hexaoxacyclooctadecane is designated as "18-crown-6." Other examples of suitable macrocyclic polyethers are 3,4-benzo-1,6,9,12,15,18,21-heptaoxacyclotricos-3-ene and 3,4-benzo-1,6,9,12,-tetra-oxacyclotetradec-3-ene. 18-Crown-6 is particularly suitable. Further suitable macrocyclic polyethers and their preparation are described in U.S. Pat. No. 3,562,295, British Pat. No. 1,108,921 and Netherlands publication No. 7602,604.

Thus, useful macrocyclic polyethers can have from 15 to 30 ring atoms in the polyether ring and consist of from 5 to 10 —O—X— units wherein X for a particular compound is either

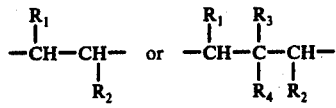

in which $R_1$ $R_2$ $R_3$ and $R_4$ are radicals independently selected from the group consisting of hydrogen and alkyl radicals having from 1 to 4 carbon atoms with the proviso that when the —O—X— units comprise

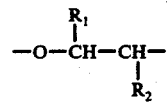

one of X can be (b). For example:
1,4,7,10,13,16-hexaoxacyclooctadecane,
1,4,7,10,13-pentaoxacyclopentadecane,
1,4,7,10,13,16,19-heptaoxacycloheneicosane,
1,4,7,10,13,16,19,22-octacyclotetracosane, and
1,4,7,10,13,16,19,22,25,27-decaoxacyclotriacontane Other, useful macrocyclic polyethers can contain 4 to 80 atoms, preferably 14–28 are ring atoms of which at least 4 and preferably 5 to 8 are oxygen atoms. Up to 10 carbon atoms can be present between one or more pairs of oxygen atoms with at least 1 aromatic nucleus attached to the polyether ring by means of vicinal carbon atoms of the aromatic nucleus. The aromatic nucleus may be optionally substituted by halogen, alkyl, cyano, amino, nitro, hydroxy and carboxy radicals. For example:
2,3-benzo-1,4,7,10-tetraoxacyclododeca-2-ene,
2,3,8,9-dibenzo-1,4,7,10-tetraoxacyclododeca-2,8-diene,
2,3,9,10-dibenzo-1,4,8,11-tetraoxacyclotetradeca-2,9-diene,
2,3,9,10-bis(t-butylbenzo)-1,4,8,11-tetraoxacyclotetradeca-2,9-diene,
2,3,8,9-dibenzo-1,4,7,10,13-pentaoxacyclopentadeca-2,8-diene,
2,3,9,10-dibenzo-1,4,8,11,14-pentaoxacyclohexadeca-2,9-diene,
2,3,11,12-dibenzo-1,4,7,10,13-pentaoxacyclooctadeca-2,11-diene,
2,3,8,9-dibenzo-1,4,7,10,13,16-hexaoxacyclooctadeca-2,8-diene,
2,3,11,12-dibenzo-1,4,7,10,13,16-hexaoxacyclooctadeca-2,11-diene,
2,3,11,12-bis(t-butylbenzo)-1,4,7,10,13,16-hexaoxacyclooctadeca-2,11-diene,
2,3,11,12-bis(2',3'-naphtho)-1,4,7,10,13,16-hexaoxacyclooccta-2,11-diene,
2,3,12,13-dibenzo-1,4,11,14-tetraoxacycloeicosa-2,12-diene,
2,3,11,12-dibenzo-1,4,7,10,13,18-hexacyclodocosa-2,11-diene,
2,3,14,15-dibenzo-1,4,7,10,13,16,19,22-octaoxacyclotetracosa-2,14-diene,
2,3-benzo-1,4,7,10,13,16-hexaoxacyclooctadeca-2-ene,
2,3,8,9,14,15-tribenzo-1,4,7,10,13,16-hexaoxacyclooctadeca-2,8,14-triene,
2,3,9,10-dibenzo-1,4,8,11,14,17-hexaoxacyclononadeca-2,9-diene,
2,3,8,9,14,15-tribenzo-1,4,7,10,13,16-hexaoxacyclononadeca-2,8,14-triene,
2,3,11,12-dibenzo-1,4,7,10,13,16,19-heptaoxacycloheneicosa-2,11-diene, 2,3,8,9,14,15-tribenzo-1,4,7,10,13,16,19-heptaoxacyclohenicosa-2,8,14-triene,
2,3,8,9,14,15-tribenzo-1,4,7,10,13,16,19,22-octaoxacyclotetracosa-2,8,14-triene,
2,3,8,9,14,15,20,21-tetrabenzo-1,4,7,10,13,16,19,22-octaoxacyclotetracosa-2,8,14-triene,
2,3,15,16-dibenzo-1,4,9,14,17,22-hexaoxacyclohexacosa-2,15-diene,
2,3-(t-butylbenzo)-1,4,7,10,13,16-hexaoxacyclooctadeca-2-ene,
2,3-benzo-1,4,7,10-13-pentaoxacyclopentadeca-2-ene,
2,3-(t-butylbenzo)-1,4,7,10,13-pentaoxacyclopentadeca-2-ene, and
2,3,16,17-dibenzo-1,4,15,18-tetraoxacyclooctacosa-2,16-diene.

Other suitable macrocyclic polyethers have the formulas

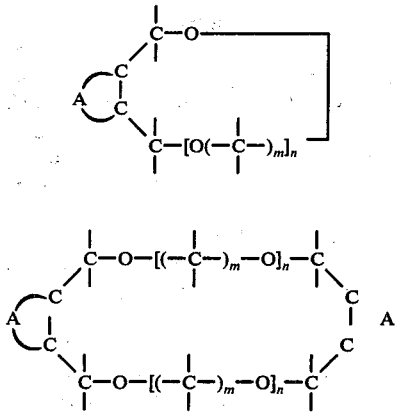

(II)

(III)

and

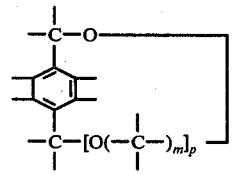

(IV)

in which formulas A and the two carbon atoms attached to A together represent a carbocyclic aromatic or hetero-aromatic group, $m$, $n$ and $p$ are integers from 2 to 10 inclusive, of at least 2 and of at least 3, respectively.

Examples of macrocyclic polyethers of formulas II, III, and IV include:
3,4-benzo-1,6,9,12,15,18,21-heptaoxacyclotricos-3-ene,
3,4-benzo-1,6,9,12-tetraoxacyclotetradec-3-ene,
3,4,17,18-dibenzo-1,6,9,12,15,20,23,26-octaoxacyclooctacos-3,17-diene,
3,4-benzo-1,6,9-trioxacycloundec-3-ene,
3,4-benzo-1,6,9,12,15-pentaoxacycloheptadec-3-ene,
3,4-benzo-1,6,9,12,15,18-hexaoxacycloeicos-3-ene,
3,4-benzo-1,6,9,12,15,18,21,24-octaoxacyclohexacos-3-ene,
3,4,14,15-dibenzo-1,6,9,12,17,20-hexaoxacyclodocos-3-ene,
3,4,17,18-dibenzo-1,6,9,12,15,20,23,26-octaoxacyclooctacos-3,17-diene,
3,4,20,21-dibenzo-1,6,9,12,15,18,23,26,29,32-decaoxacyclotetratriacont-3,20-diene,
[3,4-c]furo-1,6,9,12,15,18,21,24-octaoxacyclohexacos-3-ene,
[3,4-c]furo-1,6,9,12-tetraoxacyclotetradecane,
[3,4-c]furo-1,6,9,12,15-pentaoxacycloheptadecane,
[3,4-c]furo-1,6,9,12,15,18-hexaoxacycloeicosane,
[3,4-c]furo-1,6,9,12,15,18,21-heptaoxacyclotricosane,
[3,4-c]furo-1,6,9,12,15,18,21,24-octaoxacyclohexacosane,
3,4,14,15 difuro-1,6,9,12,17,20-hexaoxacyclodocosane,
3,4,17,18-difuro-1,6,9,12,15,20,23,26-octaoxacyclooctacosane,
3,4,20,21-difuro-1,6,9,12,15,18,23,26,29,32-decaoxacyclotetratriacontane,
[3,4-c]furo-1,6,9,12-tetraoxacyclotetradec-3-ene,
[3,4-c] [17,18-c]difuro-1,6,9,12,15,20,23,26-octaoxacyclooctacos-3,17-diene,
[3,4-c]-$2^1,5^1$-dimethylthieno-1,6,9,12,15,18-hexaoxacycloeicos-3-ene,
3,4-($4^1,5^1$-methylene-dioxybenzo)-1,6,9,12,15,18,21-heptaoxacyclotricos-3-ene,
3,6-benzo-1,8,11,14-tetraoxacyclohexadec-3,5-diene,
3,6-benzo-1,8,11,14,17,pentaoxacyclononadec-3,5-diene,
3,6-benzo-1,8,11,14,17,20-hexaoxacyclodocosa-3,5-diene,
3,6-benzo-1,8,11,14,17,20,23-heptaoxacyclopentacosa-3,5-diene,
3,6-benzo-1,8,11,14,17,20,23,26-octaoxacyclooctacosa-3,5-diene, and
3,6-benzo-1,8,11,14,17,20,23,26,29-nonaoxacyclohentriaconta-3,5-diene.

' The molar ratio of the amount of phase transfer catalyst to the amount of aromatic aldehyde of the formula ArC(O)H may vary within wide limits, but is suitably from 1:5 to 1:500. The use of low molar ratios will require a longer time to complete the reaction, whilst the use of higher molar ratios naturally increases the cost to produce a given quantity of ester. Thus, the choice of reaction time and molar ratio catalyst to aromatic aldehyde are mutually interdependent, and in any individual instance will depend on the local economic factors. Very good results are usually obtained at molar ratios from 1:10 to 1:100.

Another advantage of the process according to the present invention is that the molar ratio of the amount of (cyclo)aliphatic acyl halide to the amount of aromatic aldehyde can be kept so low that a molar excess of the halide is not or hardly not required. This molar ratio is preferably in the range of from 1.1 to 1.0. When the substantially water-immiscible aprotic solvent is a (cyclo)alkane or a mixture of (cyclo)alkanes molar ratios equal to 1.0 give excellent results.

The molar ratio of the amount of water-soluble cyanide to the amount of aromatic aldehyde is suitably from 1.5 to 1.00 and preferably from 1.3 to 1.02. By "water-soluble cyanide" is meant a water-soluble salt of hydrogen cyanide. Of the water-soluble cyanides alkail-metal cyanides and alkaline-earth-metal cyanides are preferred. Sodium cyanide is particularly preferred, because it affords the esters of the formula I in the shortest reaction time.

The temperature at which the process is conducted is suitably above 0° C and is preferably in the range of from 10° to 50° C. Very good results have been obtained at temperatures in the range of from 15° to 40° C. The process has the advantage that ambient temperatures are very suitable.

The most suitable substantially water-immiscible aprotic solvent is a (cyclo)alkane having up to 10 carbon atoms, preferably having 6 to 10 carbon atoms, or a mixture of such (cyclo)alkanes, because they allow the shortest reaction times. The use of these solvents is claimed in our concurrently filed U.S. patent application Ser. No. 765,188, filed Feb. 3, 1977. Examples of suitable (cyclo)alkanes are n-hexane, n-heptane, n-octane, n-nonane, n-decane and their isomers (for example 2-methylpentane, 3-methylpentane 2-methylhexane, 3-methylhexane and 2,4,4-trimethylpentane) and cyclohexane and methylcyclohexane. Gasolines rich in alkanes are also very suitable, for example with a boiling range at atmospheric pressure between 40° and 65° C, 60° and 80° C or 80° and 110° C. Very good results have been obtained with n-heptane and cyclohexane.

Other very suitable substantially water-immiscible aprotic solvents are aromatic hydrocarbons and chlorinated hydrocarbons, for example benzene, toluene, o-, m- and p-xylene, the trimethylbenzenes, dichloromethane, 1,2-dichloromethane, chloroform, monochlorobenzene and 1,2- and 1,3-dichlorobenzene. Very good results have been obtained with toluene.

The process according to the present invention may be conducted starting from unsaturated or saturated aqueous solutions of water-soluble cyanide and in the latter case in the presence or absence of solid water-soluble cyanide. The use of solid water-soluble cyanide is covered in our concurrently filed U.S. patent application Ser. No. 765,184, filed Feb. 3, 1977.

It has been found that when in a given case in which in successive comparable experiments less water and more solid water-soluble cyanide are applied (starting from a saturated aqueous solution of cyanide containing no solid water-soluble cyanide and keeping the total amount of water-soluble cyanide constant) the reaction time can be kept shorter and shorter, passes a minimum and then becomes longer and longer until it has become as long as in the starting case.

The use of (cyclo)alkanes in combination with aqueous solutions of cyanide in the absence of solid water-soluble cyanide allows very short reaction times. The use of aromatic hydrocarbons or chlorinated hydrocarbons in combination with aqueous solutions of cyanide in the absence of solid water-soluble cyanide needs longer reaction times, but the use of these two groups of solvents in combination with solid water-soluble cyanide allows very short reaction times. Solid water-soluble cyanide may also be used in the presence of (cyclo)alkanes, but the reaction times can already be kept very short in the absence of the former. The above-mentioned minimum reaction time is usually obtained when molar ratios of the amount of water to the total amount of water-soluble cyanide is higher than 0.05 and particularly in the range of from 0.05 to 1. For comparison it may be stated that the molar ratios of water to sodium cyanide in a saturated aqueous solution of sodium cyanide at 10° C and 35° C are 5.7 and 3.3, respectively. Consequently, extremely small amounts of water are sufficient to obtain the shortest reaction times. Furthermore, the yield of the ester of the formula I is usually very high and sometimes quantitative. In addition to the possibility of using short reaction times the use of solid water-soluble cyanide has a cost-saving effect, since smaller volumes of water can be handled.

Other examples of substantially water-immiscible aprotic solvents are dialkyl ethers and substantially water-immiscible alkanones each containing from 4 to about 8 carbon atoms, for example diethyl ether, diisopropyl ether and diisobutyl ketone. For these solvents the above-mentioned minimum reaction time can easily be determined by means of simple experiments in which the molar ratio of the amount of water to the total amount of water-soluble cyanide is varied. Mixtures of solvents, for example of alkanes and chlorinated hydrocarbons or aromatic hydrocarbons may be applied, for example of n-heptane containing up to 10% by weight of benzene and/or toluene.

The optionally substituted aromatic group Ar in the aromatic aldehyde of the formula ArC(O)H may be carbocyclic or heterocyclic. Examples of carbocyclic groups are phenyl, 1-naphthyl, 2-naphthyl and 2-anthryl group. Heterocyclic aromatic groups are derived from hetero-aromatic compounds which are defined as in Kirk-Othmer, "Encyclopedia of Chemical Technology," Second Edition, Volume 2 (1963), page 702: obtained by replacement of one or more carbon atoms of a carbocyclic aromatic compound by a hetero-atom - for example pyridine, pyrimidine, pyrazine, quinoline and isoquinoline - and also include those heterocyclic compounds having five-membered rings which show aromatic characteristics and are mentioned on page 703 of said volume, for example thiophene, pyrrole, furan, indole and benzothiophene. As an aromatic group an optionally substituted phenyl group is very suitable. Examples of substituents are hydrocarbyl and hydrocarbyloxy groups. Very good results have been obtained with phenoxybenzaldehydes, especially m-phenoxybenzaldehyde.

The group R in the formula RC(O)Hal may, for example, be an optionally substituted alkyl group. The alkyl group may be straight or branched. The alkyl groups preferably have a tertiary or quaternary carbon atom bound to the group —C(O)Hal. Examples of such alkanoyl halides are 2-methylpropanoyl chloride, 2,2-dimethylpropanoyl chloride and 2-methylbutanoyl bromide. Very good results have been obtained with 2-methylpropanoyl chloride. The alkyl group may carry as substituents, for example, hydrocarbyloxy or substituted phenyl groups, such as halophenyl or alkylphenyl. Very good results have been obtained with 1-(4-chlorophenyl)-2-methylpropyl groups. The expression "saturated cyclic hydrocarbyl group" in this patent application refers to cyclic hydrocarbyl groups in which the ring is satruated; this ring may carry substituents for example, alkyl groups of 1 to 6 carbon atoms, such as methyl, halogen atoms of atomic numbers 9 to 35, inclusive, such as chlorine, bromine or fluorine, or unsaturated side chains such as isobutenyl, dichlorovinyl or dibromovinyl. Examples of satruated cyclic hydrocarbyl groups are cyclopropyl, cyclobutyl and cyclohexyl groups. Very good results have been obtained with optionally substituted cyclopropanecarbonyl halides, particularly with 2,2,3,3-tetramethylcyclopropanecarbonyl halides and 2-(2,2-dichlorovinyl)-3,3-dimethylcyclopropanecarbonyl halides. The latter halides may have a cis or trans structure or may be a mixture of such structures and may be a pure optical isomer or a mixture of optical isomers.

The atom Hal in the formula RC(O)Hal is preferably a chlorine or bromine atom and in particular a chlorine atom.

The process according to the invention may be carried out by gradual addition of the acyl halide to a vigorously agitated, e.g., stirred, mixture of the other starting compounds (particularly recommended when R in the formula RC(O)Hal represents a 2,2,3,3-tetramethylcyclopropyl group) and often by placing together the total amounts of the starting compounds and vigorous agitating, e.g., stirring of the mixture thus formed, which is particularly recommended when R represents a 1-(4-chlorophenyl)-2-methylpropyl, an isopropyl or a 2-(2,2-dichlorovinyl)-3,3-dimethylcyclopropyl group.

The process is of particular interest to prepare pesticidally active esters, for example, when the aromatic aldehyde is 3-phenoxybenzaldehyde and the acyl halide is an aralkyl halide such as 2-(4-chlorophenyl)-3-methylbutanoyl chloride or a substituted-cyclopropanecarbonyl halide such as 2,2,3,3-tetramethylcyclopropanecarbonyl chloride or 2-(2,2-dichlorovinyl)-3,3-dimethylcyclopropanecarbonyl chloride, because the esters then formed are α-cyano-3-phenoxybenzyl, 2-(4-chlorophenyl)-3-methylbutanoate, α-cyano-3-phenoxybenzyl 2,2,3,3-tetramethylcyclopropanecarboxylate and α-cyano-3-phenoxybenzyl 2-(2,2-dichlorovinyl)-3,3-dimethylcyclopropanecarboxylate, respectively, all of which are pesticidally active compounds as disclosed in Belgian Pat. No. 801,946, U.S. Pat. No. 3,835,176 and Netherlands publication No. 7,307,130, respectively.

EXAMPLES

The Examples further illustrate the invention. All experiments were conducted at a temperature of 23° C. The sodium cyanide used consisted of particles having a largest dimension of 0.5 mm and contained 0.44% by weight of water. The molar ratio of water to sodium cyanide has been calculated taking into account the water present in the sodium cyanide and the water added, if any. For comparison it may be stated that the molar ratio of water to sodium cyanide in a saturated aqueous solution of sodium cyanide having a temperature of 23° C is 4.1. The reaction mixtures were stirred vigorously and analysed by gas-liquid chromatography to determine the yield of the ester formed. Reaction mixtures were filtered to remove precipitated sodium chloride and solid sodium cyanide, if any, and drying of solutions was carried out over anhydrous sodium sulphate. Flashing of the solvent took place in a film evaporator at a pressure of 15 mm Hg. All yields are calculated on starting aromatic aldehyde.

EXAMPLE 1

Preparation of α-cyano-3-phenoxybenzyl 2-(4-chlorophenyl)-3-methylbutanoate in the presence of n-heptane A 50 ml round-bottomed flask equipped with a magnetic stirrer was charged with 10 mmol of 3-phenoxybenzaldehyde, 10 mmol of 2-(4-chlorophenyl)-3-methylbutanoyl chloride, 12 mmol of sodium cyanide, water, a catalyst, if any, and 20 ml of n-heptane and the mixture thus formed was stirred. Two experiments were carried out in this manner, see Table I.

TABLE I

| Exp. no. | Catalyst name | amount % mol on aldehyde | Water added ml | Reaction time, h | Yield of ester, % |
|---|---|---|---|---|---|
| 1[1)] | — | — | 1.0 | 3 | 86 |
|  |  |  |  | 18 | more than 99 |
|  |  |  |  | 3 | 97 |
| 2 | 1,4,7,10,13,16-hexaoxacyclooctadecane | 2 | 1.0 | 3 | 94 |
|  |  |  |  | 18 | more than 99 |

[1)]not according to the invention.

Column 1 in Table I states the number of the experiment, column 2 the catalyst, column 4 the amount of water added to the starting mixture (excluding the water present in the sodium cyanide) and column 5 the reaction time. In none of the experiments solid NaCN was present. The yield of the desired ester is presented in column 6. The sodium cyanide was completely dissolved.

EXAMPLE 2

Preparation of α-cyano-3-phenoxybenzyl 2-(2,2-dichlorovinyl)-3,3-dimethylcyclopropanecarboxylate in the presence of n-heptane A 50 ml round-bottomed flask equipped with a magnetic stirrer was charged with 10 mmol of 3-phenoxybenzaldehyde, an amount of 2-(2,2-dichlorovinyl)-3,3-dimethylcyclopropanecarbonyl chloride, 12 mmol of sodium cyanide, water, a catalyst, if any and 20 ml of n-heptane. The mixture thus formed was stirred. Two experiments were carried out in this manner, see Table II. Column 3, 4 and 5 state the amounts of catalyst, water and acyl chloride added. The sodium cyanide was completely dissolved. The yield of the desired ester is presented in column 7.

EXAMPLE 3

Preparation of α-cyano-3-phenoxybenzyl 2-(4-chlorophenyl)-3-methylbutanoate in the presence of toluene A 50 ml round-bottomed flask equipped with a magnetic stirrer was charged with 10 mmol of 3-phenoxybenzaldehyde, 10.5 mmol of 2-(4-chlorophenyl)-3-methylbutanoyl chloride, 12 mmol of sodium cyanide and 20 ml of toluene. The mixture thus formed was stirred. The yields of the desired ester after 3 and 20 hours stirring are presented in Table III, see experiment 1.

Five other experiments were conducted in this manner, see Table III. Columns 2 and 3 in Table III state the catalyst and amount of water if any, respectively, added to the starting mixture, and column 4 states the molar ratio of water to sodium cyanide. The amount of catalyst added was 2%m in the experiments 2, 4 and 6 calculated on 3-phenoxybenzaldehyde.

TABLE II

| Exp. no. | Catalyst name | amount % mol on aldehyde | Water added ml | Acyl chloride, mmol | Reaction time, h | Yield of ester, % |
|---|---|---|---|---|---|---|
| 1[1)] | — | — | 1.0 | 10.2 | 3 | 49 |
|  |  |  |  |  | 21 | 94 |
|  |  |  |  |  | 44 | 99 |
| 2 | 1,4,7,10,13,16-hexa- | 2 | 1.0 | 10.0 | 2 | 76 |

TABLE II-continued

| Exp. no. | Catalyst name | amount % mol on aldehyde | Water added ml | Acyl chloride, mmol | Reaction time, h | Yield of ester, % |
|---|---|---|---|---|---|---|
| 1 | 2 | 3 | 4 | 5 | 6 | 7 |
| | oxacyclooctadecane | | | | 17 | 100 |

[1] not according to the invention

TABLE III

| Exp. no. | Catalyst | Water added, ml | Molar ratio water to NaCN | Reaction time, h | Yield of ester, % |
|---|---|---|---|---|---|
| 1 | 2 | 3 | 4 | 5 | 6 |
| 1[1] | none | — | 0.012[2] | 3 | 19 |
| | | | | 20 | 18 |
| 2 | 1,4,7,10,13,16-hexa-oxacyclooctadecane | — | 0.012[2] | 2 | 60 |
| | | | | 20 | 91 |
| | | | | 80 | 97 |
| 3[1] | none | 0.02 | 0.105[2] | 3 | 38 |
| | | | | 24 | 98 |
| | | | | 44 | 99 |
| 4 | 1,4,7,10,13,16-hexaoxacyclooctadecane | 0.02 | 0.105[2] | 3 | 100 |
| 5 | none | 1.00 | 4.64 | 3 | 41 |
| | | | | 24 | 87 |
| | | | | 85 | 95 |
| 6 | 1,4,7,10,13,16-hexaoxacyclooctadecane | 1.00 | 4.64 | 2 | 95 |
| | | | | 4 | 98 |
| | | | | 20 | 100 |

[1] not according to the invention.
[2] solid NaCN was present.

EXAMPLE 4

Preparation of α-cyano-3-phenoxybenzyl 2,2,3,3-tetramethylcyclopropanecarboxylate in the presence of n-heptane Methods A and B were applied to prepare the ester wanted.

Method A

A 50 ml round-bottomed flask equipped with a magnetic stirrer was charged with 10 mmol of 3-phenoxybenzaldehyde, 10 mmol of 2,2,3,3-tetramethylcyclopropanecarbonyl chloride, 12 mmol of sodium cyanide, 1.00 ml of water, a catalyst, if any, and 20 ml of n-heptane. The molar ratio of water to NaCN was 4.64, solid NaCN being absent. The catalyst was added in an amount of 0.20 mmol. The mixture thus formed was stirred for 1.5 hours and analysed.

Method B

The flask used for method A was charged with 10 mmol of 3-phenoxybenzaldehyde, 12 mmol of sodium cyanide, 10 ml of n-heptane, 1.00 ml of water and 0.20 mmol of a catalyst, if any, the molar ratio of water to NaCN being 4.64. An amount of 10 mmol of 2,2,3,3-tetramethylcyclopropanecarbonyl chloride dissolved in 10 ml of n-heptane was introduced into the flask during a period of 70-75 min. The yield of the ester was determined at the end of this period.

Two experiments were carried out in this manner. Table IV states the catalyst used, if any. This Table also presents the yield of the desired ester.

TABLE IV

| Exp. no. | Catalyst | Yield of ester, % Method A | Method B |
|---|---|---|---|
| 1* | none | 17 | 40 |
| 2 | 1,4,7,10,13,16-hexaoxa-cyclooctadecane | 18 | 97 |

*not according to the invention

The amounts of the catalyst used was 2%m in the experiment 2, calculated on 3-phenoxybenzaldehyde.

We claim:

1. A process for the preparation of an ester of the formula

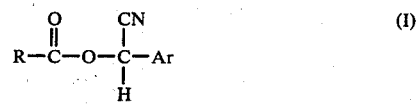

(I)

wherein Ar represents a phenoxy substituted phenyl group and R an alkyl group optionally substituted by halophenyl or alkylphenyl or a cyclopropyl group optionally substituted by alkyl, halogen, isobutenyl, dichlorovinyl or dibromovinyl, which process comprises contacting an aromatic aldehyde of the formula ArC(O)H and a (cyclo)aliphatic aryl halide of the formula RC(O)Hal, in which formulas Ar and R have the same meaning as in the formula I and Hal represents a halogen atom having an atomic number from 9 to 53, inclusive, with water, a water-soluble cyanide, a substantially water-immiscible aprotic solvent and a macrocyclic polyether phase transfer catalyst containing a total of from 4 to 80 atoms and 14 to 28 ring atoms at least 4 of which are oxygen atoms and recovering the desired ester from the reaction mixture.

2. A process according to claim 1, in which the molar ratio of the amount of phase transfer catalyst to the amount of aromatic aldehyde of the formula ArC(O)H is from 1:5 to 1:500.

3. A process according to claim 1, which is conducted at a temperature in the range of from 10° to 50° C.

4. A process according to claim 1, in which the total amount of the water-soluble cyanide is dissolved in the water.

5. A process according to claim 4, in which the substantially water-immiscible aprotic solvent is a (cyclo)alkane or a mixture of (cyclo)alkanes.

6. A process according to claim 5, in which the alkane is n-heptane.

7. A process according to claim 5, in which the (cyclo)alkane is cyclohexane.

8. A process according to claim 1, which is conducted in the presence of solid water-soluble cyanide.

9. A process according to claim 8, in which the substantially water-immiscible aprotic solvent is an aromatic hydrocarbon or a mixture of aromatic hydrocarbons.

10. A process according to claim 9, in which the aromatic hydrocarbon is toluene.

11. A process according to claim 8, in which the substantially water-immiscible aprotic solvent is a chlorinated hydrocarbon.

12. A process according to claim 1, in which the starting molar ratio of the amount of water to the total amount of water-soluble cyanide is higher than 0.05.

13. A process according to claim 12, in which the starting molar ratio of the amount of water to the total amount of water-soluble cyanide is in the range of from 0.05 to 1.

14. A process according to claim 1, in which the molar ratio of the amount of (cyclo)aliphatic acyl halide of the formula RC(O)Hal to the amount of the aromatic aldehyde of the formula ArC(O)H is in the range of from 1.1 to 1.0.

15. A process according to claim 14, in which the molar ratio of the amount of (cyclo)aliphatic acyl halide of the formula RC(O)Hal to the amount of the aromatic aldehyde of the formula ArC(O)H is 1.0.

16. A process according to claim 1, in which the water-soluble cyanide is sodium cyanide.

17. A process according to claim 1, in which Hal in the formula RC(O)Hal represents a chlorine atom.

18. A process according to claim 1, in which the group R in the formula RC(O)Hal is an optionally substituted (cyclo)alkyl group having a tertiary or quaternary carbon atom bound to the group —C(O)Hal.

19. A process according to claim 18, in which the group R is a 1-(4-chlorophenyl)-2-methylpropyl group or an isopropyl group.

20. A process according to claim 18, in which the group R is an optionally substituted cyclopropyl group.

21. A process according to claim 20, in which the group R is a 2,2,3-tetramethylcyclopropyl group or a 2-(2,2-dichlorovinyl)-3,3-dimethylcyclopropyl group.

22. A process according to claim 19, which is carried out by forming a mixture of the total amounts of the aromatic aldehyde, the (cyclo)aliphatic acyl halide, the water, the water-soluble cyanide and the substantially water-immiscible aprotic solvent, and stirring the mixture thus formed.

23. A process according to claim 21, which is carried out by gradual addition of a 2,2,3,3-teteramethylcyclopropanecarbonyl halide to a stirred mixture of the aromatic aldehyde, the water, the water-soluble cyanide and the substantially water-immiscible aprotic solvent.

24. A process according to claim 1, wherein the macrocyclic polyether catalyst is 1,4,7,10,13,16-hexaoxacyclooctadecane, 3,4-benzo-1,6,9,12,15,18,21-heptaoxacyclotricos-3-ene or 3,4-benzo-1,6,9,12-tetraoxacyclotetradec-3-ene.

25. A process according to claim 1 wherein the macrocyclic polyether catalyst contains 5 to 8 ring oxygen atoms.

26. A process according to claim 25 wherein the water soluble cyanide is sodium cyanide and the solvent is an alkane, a cycloalkane, an aromatic hydrocarbon, chlorinated hydrocarbon or a mixture thereof.

27. A process according to claim 26 which is conducted at a temperature in the range of from 10° C to 50° C, with the molar ratio of the amount of (cyclo)aliphatic acyl halide to the amount of the aromatic aldehyde is from 1.1 to 1.0 and in which the starting molar ratio of the amount of water to the total amount of water-soluble cyanide is higher than 0.05.

28. A process according to claim 27 wherein the macrocyclic polyether catalyst is 1,4,7,10,13,16-hexaoxacyclooctadecane, 3,4-benzo-1,6,9,12,15,18,21-heptaoxacyclotricos-3-ene or 3,4-benzo-1,6,9,12-tetraoxacyclotetradec-3-ene.

29. A process according to claim 28 wherein the ester of formula I is α-cyano-3-phenoxybenzyl 2-(4-chlorophenyl)-3-methylbutanoate.

* * * * *